United States Patent
Young et al.

(10) Patent No.: US 12,246,040 B2
(45) Date of Patent: Mar. 11, 2025

(54) HUMAN HOMOGENEOUS AMNIOTIC FLUID STEM CELL LINES AND USES THEREOF

(71) Applicants: Bruce K. Young, New York, NY (US); Michael K. Chan, Brooklyn, NY (US)

(72) Inventors: Bruce K. Young, New York, NY (US); Michael K. Chan, Brooklyn, NY (US)

( * ) Notice: Subject to any disclaimer, the term of this patent is extended or adjusted under 35 U.S.C. 154(b) by 627 days.

(21) Appl. No.: 16/568,707

(22) Filed: Sep. 12, 2019

(65) Prior Publication Data

US 2020/0101116 A1    Apr. 2, 2020

Related U.S. Application Data

(60) Provisional application No. 62/739,262, filed on Sep. 30, 2018.

(51) Int. Cl.
| | |
|---|---|
| A61K 35/50 | (2015.01) |
| C12N 5/073 | (2010.01) |
| C12N 5/074 | (2010.01) |
| G01N 33/50 | (2006.01) |

(52) U.S. Cl.
CPC ............ A61K 35/50 (2013.01); C12N 5/0605 (2013.01); C12N 5/0607 (2013.01); G01N 33/5014 (2013.01); G01N 33/5073 (2013.01); G01N 2500/04 (2013.01); G01N 2500/10 (2013.01)

(58) Field of Classification Search
CPC .... A61K 35/50; C12N 5/0605; C12N 5/0607; C12N 5/0619; C12N 5/0654; C12N 5/0655; C12N 2503/02; C12N 2506/03; G01N 33/5014; G01N 33/5073; G01N 2500/04; G01N 2500/10; A61P 9/10; A61P 17/02; A61P 21/00; A61P 25/28
See application file for complete search history.

(56) References Cited

FOREIGN PATENT DOCUMENTS

WO    WO-2007046775 A1 * 4/2007 ............. A61K 35/32

OTHER PUBLICATIONS

Sun et al. Amniotic fluid stem cells provide considerable advantages in epidermal regeneration: B7H4 creates a moderate inflammation microenvironment to promote wound repair. Sci Rep 5, 11560 (2015) (Year: 2015).*
Chen et al. Heterogeneity of Stem Cells in Human Amniotic Fluid 2014 J Regen Med vol. 3 Issue: 1 (Year: 2014).*
Siegel et al. Stem Cells in Amniotic Fluid as New Tools to Study Human Genetic Diseases, 2007 Stem Cell Rev 3:256-264 (Year: 2007).*
Ma et al. Clone-derived human AF-amniotic fluid stem cells are capable of skeletal myogenic differentiation in vitro and in vivo J Tissue Eng Regen Med 2012;6: 598-613. (Year: 2012).*
ThermofisherScientific "Understand the Basics of Fetal Bovine Serum (FBS)" 2020 (Year: 2020).*
Phermthai et al. A novel method to derive amniotic fluid stem cells for therapeutic purposes; BMC Cell Biology 2010, 11:79 (Year: 2010).*
Bai, J., Hu, Y., Wang, Y.R., Liu, L.F., Chen, J., Su, S.P. and Wang, Y., 2012. Comparison of human amniotic fluid-derived and umbilical cord Wharton's Jelly-derived mesenchymal stromal cells: Characterization and myocardial differentiation capacity. Journal of geriatric cardiology: JGC, 9(2), p. 166. (Year: 2012).*
Ovens, L. and Irving, S., 2018. Advances in wound cleansing: an integrated approach. Wounds UK, 14(1). (Year: 2018).*
Spitzhorn et al. 2017. Isolation and molecular characterization of amniotic fluid-derived mesenchymal stem cells obtained from caesarean sections. Stem cells international, 2017(1), p. 5932706. (Year: 2017).*
Kim, J., Lee, Y., Kim, H., Hwang, K.J., Kwon, H.C., Kim, S.K., Cho, D.J., Kang, S.G. and You, J., 2007. Human amniotic fluid-derived stem cells have characteristics of multipotent stem cells. Cell proliferation, 40(1), pp. 75-90. (Year: 2007).*
Bonaventura, G., Chamayou, S., Liprino, A., Guglielmino, A., Fichera, M., Caruso, M. and Barcellona, M.L., 2015. Different tissue-derived stem cells: a comparison of neural differentiation capability. PloS one, 10(10), p. e0140790. (Year: 2015).*
Sedrakyan et al. 2017. Amniotic fluid stem cell-derived vesicles protect from VEGF-induced endothelial damage. Scientific reports, 7(1), p. 16875. (Year: 2017).*
Chen Z, et al., Heterogeneity of Stem Cells in Human Amniotic Fluid, J. Regen. Med. 3:1, 2014, United States.
Wilson et al., Stem Cells International, vol. 2012, Article ID 485590 (2012), United States.

* cited by examiner

Primary Examiner — Jeremy C Flinders
Assistant Examiner — Masudur Rahman
(74) Attorney, Agent, or Firm — ENTRALTA PLLC; Peter D. Weinstein; James F. Fleming

(57) ABSTRACT

Homogeneous human amniotic fluid stem cell clones are provided. The clones serve as direct bioassays to test the effect of drugs, nutraceuticals, vitamins and toxic agents on fetus growth, differentiation and development, and may be administered in form of pharmaceutical compositions for reconstructive engineering and for the treatment of cardiac, neurological and osteoarthritic diseases.

10 Claims, 1 Drawing Sheet

HUMAN HOMOGENEOUS AMNIOTIC FLUID STEM CELL LINES AND USES THEREOF

RELATED APPLICATION DATA

This application claims priority to U.S. Provisional Application No. 62/739,262, filed Sep. 30, 2018, the content of which is hereby incorporated by reference in its entirety for all purposes.

FIELD

Homogeneous human amniotic fluid stem cell lines, and their use in bioassays, reconstructive engineering and in methods for treating cardiac, neurological and osteoarthritic diseases are disclosed. The disclosed homogeneous human amniotic fluid clones are easily cultured and expanded, remain viable over many passages, are not tumorigenic, and consistently express embryonic stem cell markers CD90 (95-99% expression), SSEA4 (27% expression) and Tra-1-60 (5-10% expression), as well as transcription factors specific for human embryonic stem cells that are associated with maintenance of undifferentiated state and pluripotency, even after numerous passages.

BACKGROUND

Stem cells have great potential for therapies in a wide range of conditions. Bone marrow, peripheral blood cells, umbilical cord cells and embryonic tissue have been examined as potential sources of stem cells in human therapies, as have adult cells restored to pluripotency by genetic manipulation. There are, however, several problems with the use of these cells. In particular, these cells are limited in number, are difficult to maintain in culture and expand, and are prone to induce tumorigenesis. Furthermore, ethical concerns have limited embryonic sources and cord blood collection. In addition, pharmacological agents used in pregnancy are not usually tested on pregnant women for their potential effects on the fetus due to ethical concerns. Thus, the study of drug effects has been limited to measurements in maternal and umbilical cord blood and neonatal assessments.

Amniotic fluid contains significant quantities of cells derived from embryonic tissues, such as the skin and the respiratory, urinary and gastrointestinal tracts, as well as pluripotent stem cells. Amniotic fluid cells obtained from second trimester pregnancies undergoing genetic amniocentesis appear to be valuable source of multipotential stem cells and are not subject to the problems encountered with the use of other stem cells. They are easily grown and multiplied, they are not tumorigenic, and they are routinely sampled and grown in tissue culture for genetic testing, so they are not controversial. However, amniotic fluid stem cells are highly heterogeneous, as they are subject to extensive individual variations. This heterogeneity makes it necessary to use multiple samples from different individuals to perform research, assess the effect of drugs on tissue differentiation and determine potential regenerative medicine.

A need exists for amniotic fluid clonal stem cell lines that are derived from a single cell, maintain their stemness throughout their culture, and can be effectively used to develop standard drug bioassays and potential therapies.

The present application presents a solution to the aforementioned challenges, by providing human amniotic fluid clonal stem cell lines that are consistently homogeneous and are amenable for use as drug bioassays and platforms for regenerative medicine.

SUMMARY

It is shown herein that homogeneous amniotic fluid clonal stem cell lines retain their stemness and pluripotency characters through many passages and after cryopreservation, consistently present 99 to 100% expression of the embryonic stem cell marker CD90, can differentiate into neuronal, cartilage and bone tissue, and can be used as a standardized test to determine the effect of drugs and toxic agents on human fetal cell growth and their ability to differentiate. Based on these findings, homogeneous human amniotic fluid clonal stem cell lines are provided. The homogeneous human amniotic fluid clonal stem cell lines consist of one or more clones of homogeneous amniotic fluid stem cells that have a normal karyotype, do not form tumors in a host, are capable of self-renewal, and are capable of differentiation to cells of endodermal, ectodermal and mesodermal lineages.

The disclosed homogeneous human amniotic fluid clonal stem cell lines consistently express CD90, SSEA4 and TRA-1-60 stem cell surface markers and embryonic transcription factors for pluripotency OCT4, Nanog, SOX-2, REX-1, CD117, CD15, CD44, CD29, CD9, CD73 AND CD133. In some examples, 99% to 100% of the homogeneous amniotic fluid stem cells consistently express CD90, 27% of the homogeneous amniotic fluid stem cells consistently express SSEA4 and 5-10% of the homogeneous amniotic fluid stem cells consistently express TRA-1-60 after five passages or more.

Also provided herein are cell cultures, which comprise the disclosed one or more homogeneous human amniotic fluid clonal stem cell lines and a medium that supports proliferation of the homogeneous amniotic fluid stem cells.

Additionally provided herein are bioassays, which comprise cell cultures of the disclosed homogeneous human amniotic fluid clonal stem cell lines. In some embodiments, the bioassays may include dose-responsive reporter genes driven by inducible promoters, or labeling antibodies.

Also provided herein is a method for screening an agent for its effect on a human fetus, wherein the method comprises: (1) culturing samples of the disclosed bioassays and incubating the samples (a) in absence of the agent; (b) after a short, single exposure to the agent; or (c) in continuous presence of the agent, to produce three-dimensional spherical colonies of the disclosed homogeneous human amniotic fluid clonal stem cell lines; (2) determining the agent's effect on each sample by assessing changes in proliferation or differentiation of the homogeneous human amniotic fluid clonal stem cells brought about by the agent; and (3) if an effect is detected, quantifying the agent's effect by dose effect and/or gene expression.

In some embodiments, the agent is a drug, a compound, a vitamin, an omega-3 fatty acid, a supplement, a food additive, a toxic agent, or a potential teratogen. Toxic agents may include, but are not limited to, an opioid, lithium, marijuana, cocaine or a radiation. Potential teratogens may include, but are not limited to, an ACE inhibitor, a blood thinner, a hormone, an anti-depressant, a seizure medication, an anti-rheumatic agent, streptomycin, valproic acid, or thalidomide.

Also provided herein are pharmaceutical compositions that comprise the disclosed one or more homogeneous human amniotic fluid clonal stem cell lines. In some embodiments, the pharmaceutical compositions may comprise one or more of a pharmaceutically acceptable excipient, a pharmaceutically acceptable carrier, a diluent, adjuvant, stabilizer, emulsifier, preservative, colorant, or buffer. In some embodiments, the pharmaceutical compositions may additionally comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an antibacterial agent or an antifungal agent.

Additionally provided herein are methods of repairing a tissue or replacing an organ in a subject in need thereof, wherein the methods comprise administering to the subject a pharmaceutical composition that comprises the disclosed homogeneous human amniotic fluid clonal stem cell lines to regenerate the tissue or organ, thereby repairing the tissue or replacing the organ in the subject. In some embodiments, the tissue or organ may be part of the subject's respiratory tract, gastrointestinal tract, salivary glands, cardiovascular system, liver, pancreas, bone marrow, joints, bones, cartilage, knee, skeleton, central nervous system or skin. Administration of the pharmaceutical composition may be topical, transdermal, mucosal, sub-mucosal, muscular, sub-muscular, by inhalation, parenteral or intravenous administration.

In other embodiments, provided herein are methods of managing or treating neonatal encephalopathy, traumatic brain injury or ischemia in a subject in need thereof, wherein the methods comprise administering to the subject a pharmaceutical composition that comprises the disclosed homogeneous human amniotic fluid clonal stem cell lines, thereby managing or treating neonatal encephalopathy, traumatic brain injury or ischemia in the subject.

In yet other embodiments, provided herein are methods of treating, controlling or managing diabetes in a subject with a damaged pancreas, wherein the methods comprise regenerating pancreatic islets by administering to the subject a pharmaceutical composition that comprises the disclosed homogeneous human amniotic fluid clonal stem cell lines, thereby treating, controlling or managing diabetes in the subject.

In additional embodiments, provided herein are methods of treating, controlling or managing a cardiovascular disease in a subject in need thereof, wherein the methods comprise regenerating cardiac tissue and vascularization by injecting into the subject's cardiac tissue a pharmaceutical composition that comprises the disclosed homogeneous human amniotic fluid clonal stem cell lines, thereby treating, controlling or managing the cardiovascular disease.

In yet other embodiments, provided herein are methods of treating, controlling or managing a progressive neurodegenerative disease in a subject in need thereof, wherein the methods comprise regenerating neurons by injecting into the subject's brain a pharmaceutical composition that comprises the disclosed homogeneous human amniotic fluid clonal stem cell lines, thereby treating, controlling or managing the progressive neurodegenerative disease. Progressive neurodegenerative diseases may include, but are not limited to, Alzheimer's disease, Huntington's disease, amyotrophic lateral sclerosis, multiple sclerosis, multiple system atrophy, or Parkinson's disease.

In additional embodiments, provided herein are methods of treating, controlling or managing muscular dystrophy in a subject in need thereof, wherein the methods comprise regenerating myogenic cells by administering to the subject a pharmaceutical composition that comprises the disclosed homogeneous human amniotic fluid clonal stem cell lines, thereby treating, controlling or managing muscular dystrophy.

Also provided herein are methods of managing, controlling or treating a peripheral nerve or muscle injury in a subject in need thereof, wherein the methods comprise parenterally administering to the subject a pharmaceutical composition that comprises the disclosed homogeneous human amniotic fluid clonal stem cell lines to regenerate the peripheral nerve or muscle, thereby managing, controlling or treating a peripheral nerve or muscle injury in the subject.

In other embodiments, provided herein are methods of regenerating skin, repairing a burn or healing a wound in a subject in need thereof, wherein the methods comprise topically or parenterally administering to the subject a pharmaceutical composition that comprises the disclosed homogeneous human amniotic fluid clonal stem cell lines, thereby regenerating the skin, repairing the burn or healing the wound in the subject.

In yet other embodiments, provided herein are methods of controlling, managing or treating arthritis in a subject in need thereof, wherein the methods comprise administering to the subject a pharmaceutical composition that comprises the disclosed homogeneous human amniotic fluid clonal stem cell lines, thereby controlling, managing or treating arthritis.

In some embodiments, the pharmaceutical compositions administered by the disclosed methods may comprise one or more of a pharmaceutically acceptable excipient, pharmaceutically acceptable carrier, a diluent, adjuvant, stabilizer, emulsifier, preservative, colorant, or buffer. In some embodiments, the pharmaceutical compositions administered by the disclosed methods may optionally comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an antibacterial agent or an antifungal agent.

The foregoing and other features of the disclosure will become more apparent from the following detailed description of several embodiments.

BRIEF DESCRIPTION OF THE DRAWINGS

FIG. 1 shows a white mice graft onto a wound area treated with $CD90^+$ amniotic fluid stem cloned cells in a black mouse. The graft looks healthy and hair is growing on the graft treated with clonal amniotic fluid stem cells, indicating enhanced vascularization.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Administer or Apply: To provide or give a subject a composition, such as a pharmaceutical composition, by an effective route. Exemplary routes of include, but are not limited to, topical, transdermal, muscular, intramuscular, sub-muscular, inhaled, parenteral, intravenous, mucosal, or sub-mucosal routes. The cells may be applied in a scaffold of various materials appropriate to the site or organ, or tissue being repaired, replaced, or regenerated, for example but not limited to a collagen or hydrogel matrix. The terms "administer" or "apply" also include exposing a cell culture or a clone to a composition, such as a pharmaceutical composition, in vitro or ex vivo.

Alzheimer's Disease (AD): An irreversible, progressive brain disorder that slowly destroys memory and thinking skills, and eventually the ability to carry out the simplest tasks. In most people with Alzheimer's, symptoms first appear in their mid-60 s. AD is currently ranked as the sixth leading cause of death in the United States, and it is the most common cause of dementia among older adults. AD is associated with the formation of β amyloid plaques and neurofibrillary tangles of the tau protein in the brain and the loss of connections between neurons in the brain. The damage initially appears to take place in the hippocampus, and as more neurons die, additional parts of the brain are affected and begin to shrink. Memory problems are typically one of the first signs of cognitive impairment related to Alzheimer's disease. As AD progresses, memory loss confusion and inability to recognize familiar faces grow worse. Ultimately, plaques and tangles spread throughout the brain, and brain tissue shrinks significantly. Causes of AD probably include a combination of genetic, environmental, and lifestyle factors. These plaques and tangles in the brain are still considered some of the main features of Alzheimer's disease. Another feature is the loss of connections between nerve cells (neurons) in the brain. Neurons transmit messages between different parts of the brain, and from the brain to muscles and organs in the body.

Amyotrophic Lateral Sclerosis (ALS): A progressive neurodegenerative disease that affects motor neurons in the brain and the spinal cord, with consequent muscle degeneration and atrophy. Sporadic ALS, the most common form of the disease in the U.S., accounts for 90 to 95 percent of all cases. Familial ALS (FALS) is genetically inherited and it accounts for 5 to 10 percent of all cases in the U.S. There is no cure for ALS.

Analog: A compound having a structure similar to another, but differing from it, for example, in one or more atoms, functional groups, or substructure.

Anesthetic agent: An active agent that causes reduction or loss of sensation.

Amniotic fluid: A protective liquid contained in the amniotic sac and surrounding the developing fetus in the uterus. It provides mechanical protection and it facilitates the exchange of nutrients required for fetal growth and health. The composition of amniotic fluid changes with gestational age.

Antagonist: A molecule that, upon binding to a cell receptor, competes and/or interferes with one or more ligands binding the same receptor, and thus reduces or prevents a response elicited by those ligands.

Antibiotic: A chemical substance capable of treating bacterial infections by inhibiting the growth of, or by destroying existing colonies of bacteria and other microorganisms.

Antibody: An immunoglobulin capable of specifically binding a target molecule, such as a carbohydrate, a polynucleotide, a lipid, or a polypeptide, via one or more antigen recognition sites, located in the variable region of the immunoglobulin molecule. The term "antibody" includes polyclonal and monoclonal antibodies, fragments thereof, such as Fab, Fab', $F(ab')_2$ and Fv, single chain variable fragments (ScFv), mutants thereof, fusion proteins comprising an antibody portion, and any other modified configuration of the immunoglobulin molecule that comprises an antigen recognition site. Antibodies can be distinguished into five major classes, IgA, IgD, IgE, IgG, and IgM, according to the amino acid sequence of the constant domain in their heavy chains. Monoclonal antibodies are obtained from a substantially homogeneous population of antibodies, and specifically target a single epitope (determinant) of an antigen. Polyclonal antibodies target different epitopes on the antigen. The heavy and light chains of an antibody each comprise a variable region and a constant region. The variable regions of the heavy and light chain each consist of four framework regions (FR) connected by three complementarity-determining regions (CDRs), also known as hypervariable regions. The CDRs in each chain are held together in close proximity by the FRs and form the antibody's antigen-binding site. The constant regions of the heavy and light chains of an antibody provide structural stability and are not involved in antigen binding.

Antibody-Dependent Cell-Mediated Cytotoxicity (ADCC): A cell-mediated reaction in which nonspecific cytotoxic cells that express Fc receptors (FcRs), such as natural killer (NK) cells, neutrophils, and macrophages, recognize bound antibody on a target cell and subsequently cause lysis of the target cell.

Anti-Fungal Agent: An active agent capable of inhibiting the growth of or destroying fungi.

Anti-inflammatory agent: An active agent that reduces inflammation and swelling.

Anti-Oxidant: An active agent that inhibits oxidation or reactions promoted by oxygen or peroxides.

Anti-Protozoal Agent: An active agent capable of inhibiting the growth of or destroying protozoa microorganisms.

Antipruritic Agent: An active agent that reduces, eliminates or prevents itching.

Anti-Viral Agent: An active agent that inhibits the replication of or destroys viruses.

Binding Site or Binding Domain: A region on a protein, DNA or RNA, to which specific molecules and/or ions (ligands) may form a chemical bond. Characteristics of binding sites are chemical specificity, a measure of the types of ligands that will bond, and affinity, which is a measure of the strength of the chemical bond.

Bioassay: An analytical method to determine safety, concentration or potency of a substance by its effect on living cells or tissues. A bioassay may involve the application of a stimulus, such as a drug, to a subject, a tissue or a cell line, to determine a particular effect of the stimulus on the subject, tissue or cell line, such as a change in cell proliferation or differentiation, growth, survival and potential for teratogenicity.

Bone: A rigid organ that constitutes part of the vertebrate skeleton. Bones support and protect the various organs of the body, produce red and white blood cells, store minerals, provide structure and support for the body, and enable mobility. Bone tissue is a hard tissue containing a honeycomb-like matrix and different types of bone cells. Osteoblasts and osteocytes are involved in the formation and mineralization of bone, and osteoclasts are involved in the resorption of bone tissue. Modified (flattened) osteoblasts become the lining cells that form a protective layer on the bone surface. The mineralized matrix of bone tissue comprises ossein and bone mineral. Ossification in the fetus occurs by intramembranous ossification, which involves the formation of bone from connective tissue, and endochondral ossification, which involves the formation of bone from cartilage.

Cancer: A condition characterized by unregulated cell growth. Examples of cancer include, but are not limited to, squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, thyroid cancer, testicular cancer, esophageal cancer, and various types of head and neck cancer.

Cartilage: An avascular and aneural tissue that covers and protects the ends of long bones at the joints. It is a structural component of the rib cage, the ear, the nose, the bronchial tubes, the intervertebral discs, and the articulating surfaces of joints. It is more widespread in the infant skeleton, and it is replaced by bone during growth. The matrix of cartilage is made up of chondrin. The cartilage is composed of chondrocytes, which produce collagenous extracellular matrix, rich in proteoglycan and elastin fibers. Cartilage is classified as elastic cartilage, hyaline cartilage and fibrocartilage, based on relative amounts of collagen and proteoglycan. In embryogenesis, the skeletal system is derived from the mesoderm germ layer. Chondrogenesis is the process by which cartilage is formed from condensed mesenchyme tissue, with consequent differentiation into chondroblasts and formation of the extracellular matrix. Cartilage growth consists mostly of the maturing of immature cartilage to a more mature state. The division of cells within cartilage occurs very slowly, and thus growth in cartilage is usually not based on an increase in size or mass of the cartilage.

CD9 (Cluster of Differentiation 9): A cell-surface glycoprotein member of the transmembrane 4 superfamily, also known as the tetraspanin family, characterized by the presence of four hydrophobic domains. Tetraspanins are cell surface glycoproteins with four transmembrane domains that form multimeric complexes with other cell surface proteins and are involved in many cellular processes including differentiation, adhesion, and signal transduction.

CD15 (Cluster of Differentiation 15): A carbohydrate adhesion molecule, also known as 3-fucosyl-N-acetyl-lactosamine and SSEA-1 (stage-specific embryonic antigen 1). It is a marker for pluripotent stem cells and it mediates phagocytosis and chemotaxis.

CD29 (Cluster of Differentiation 29): A cell surface receptor, also known as Integrin beta-1 (ITGB1), which in humans is encoded by the ITGB gene. This integrin associates with integrins alpha 1 and 2 to form integrin complexes which function as collagen receptors.

CD44 (Cluster of Differentiation 44): A cell-surface glycoprotein involved in cell-cell interactions, cell adhesion and migration. It is a receptor for hyaluronic acid (HA) and can also interact with other ligands, such as osteopontin, collagens, and matrix metalloproteinases (MMPs).

CD73 (Cluster of Differentiation 73): A glycosyl-phosphatidylinositol (GPI)-linked 70-kDa cell surface enzyme encoded by the NT5E gene, also known as ecto-5'-nucleotidase.

CD90 (Cluster of Differentiation 90): A 25-37 kDa glycophosphatidylinositol (GPI)-linked glycoprotein, also known as Thyl, expressed by stem cells, endothelial cells, hematopoietic stem cells and neurogenic cells.

CD117 (Cluster of Differentiation 117): A receptor tyrosine kinase protein, also known as proto-oncogene c-Kit or tyrosine-protein kinase Kit, which in humans is encoded by the KIT gene and is expressed on the surface of hematopoietic stem cells.

CD133 (Cluster of Differentiation 133): An antigen, also known as prominin-1, which in humans is encoded by the PROM1 gene and is expressed on the surface of hematopoietic stem cells.

Cell line: A cell culture developed from a single cell and consisting of cells with a uniform genetic makeup.

Chemotherapeutic agent or Chemotherapy: A chemical agent with therapeutic usefulness in the treatment of diseases characterized by abnormal cell growth. Such diseases include tumors, neoplasms, and cancer. In one example, a chemotherapeutic agent is a radioactive compound. In one example, a chemotherapeutic agent is a biologic, such as a monoclonal antibody. In some examples, a subject treated with an active agent using the disclosed methods, is, will be, or was previously treated with chemotherapy.

Clone: A group of identical cells that are derived from the same cell

Collagen: Major insoluble fibrous protein in the extracellular matrix and in connective tissue. Types I, II, and III collagen, which constitutes 80-90% of collagen in the human body, pack together to form long thin fibrils of similar structure. Type IV collagen forms a two-dimensional reticulum. Type I collagen is found in the skin, tendon, vasculature, organs, and bones. Type II collagen is found in the cartilage. Type III collagen is found in reticulate. Type IV collagen is found in the basal lamina. Type V collagen is found in the hair and placenta. All collagens contain three-stranded helical segments of similar structure. The triple-helical structure of collagen arises from an unusual abundance of three amino acids: glycine, proline, and hydroxyproline. These amino acids make up the characteristic motif Gly-Pro-X, where X can be any amino acid. The side chain of glycine, an H atom, is the only one that can fit into the three-stranded helix. Hydrogen bonds linking the peptide bond NH of a glycine residue with a peptide carbonyl (C=O) group in an adjacent polypeptide help hold the three chains together. The peptidyl-proline and peptidyl-hydroxyproline bonds enable each polypeptide chain to fold into a helix, such that three polypeptide chains can twist together to form a three-stranded helix.

Contacting: Placement in direct physical association; includes both in solid and liquid form. Contacting can occur in vitro with isolated cells (for example in a tissue culture dish or other vessel), ex vivo with cells or tissues isolated from an organism, or in vivo by administering an active agent to a subject.

Control: A reference standard. In some examples, a control is a known value or range of values, such as one indicative of the presence or the absence of a disease. In some examples, a control is a value or range of values, indicating a response in the absence of a therapeutic agent.

Cross-linked: A composition containing intramolecular and/or intermolecular crosslinks, whether arising through covalent or non-covalent bonding. "Non-covalent" bonding includes both hydrogen bonding and electrostatic (ionic) bonding.

Cytokine: A substance released by one cell population that acts on another cell as intercellular mediator. Examples of cytokines include, but are not limited to, lymphokines, monokines; interleukins (its) such as IL-1, IL-1α, IL-2, IL-3, IL-4, IL-5, IL-6, IL-7, IL-8, IL-9, IL-11, IL-12, IL-15, including PROLEUKTIN® rIL-2; a tumor necrosis factor such as TNF-α or TNF-β; and other polypeptide factors including LIF and kit ligand (KL).

Cytotoxic agent: A substance that inhibits or prevents the function of cells and/or causes destruction of cells. Cytotoxic agents include, but are not limited to, radioactive isotopes, chemotherapeutic agents, and toxins, such as small molecule toxins or enzymatically active toxins of bacterial, fungal, plant or animal origin, including fragments and/or variants thereof.

Differentiation: the process by which an unspecialized cell acquires the features of a specialized cell such as a heart, liver, lung, pancreas or muscle cell. When a cell differentiates into a mesodermal, ectodermal or endodermal lineage, the cell becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into an ectodermal lineage or give rise to specific ectodermal cells include, but are not limited to, cells that are epidermal cells, neurogenic cells, and neurogliagenic cells. Examples of cells that differentiate into an endodermal lineage or give rise to specific endodermal cells include, but are not limited to, cells that are alveolargenic, epatogenic, and pancreatogenic.

Domain: A distinct functional and/or structural unit of a protein. A conserved domain refers to a domain that has been conserved and in which the physico-chemical properties of the original residues have been preserved during evolution.

Drug or Active Agent: A chemical substance or compound that induces a desired pharmacological or physiological effect, and includes therapeutically effective, prophylactically effective, or systematically effective agents. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like. Suitable active agents that may be tested or incorporated into pharmaceutical compositions include, but are not limited to, adrenergic agents; adrenocortical steroids; adrenocortical suppressants; alcohol deterrents; aldosterone antagonists; amino acids; ammonia detoxicants; anabolic agents; analeptic agents; analgesic agents; androgenic agents; anesthetic agents; anorectic compounds; anorexic agents; antagonists; anterior pituitary activators and anterior pituitary suppressants; anti-acne agents; anti-adrenergic agents; anti-allergic agents; anti-amebic agents; anti-androgen agents; anti-anemic agents; anti-anginal agents; anti-anxiety agents; anti-arthritic agents; anti-asthmatic agents and other respiratory drugs; anti-atherosclerotic agents; anti-bacterial agents; anti-cancer agents, including antineoplastic drugs, and anti-cancer supplementary potentiating agents; anticholinergics; anticholelithogenic agents; anti-coagulants; anti-coccidal agents; anti-convulsants; anti-depressants; anti-diabetic agents; anti-diarrheals; anti-diuretics; antidotes; anti-dyskinetics agents; anti-emetic agents; anti-epileptic agents; anti-estrogen agents; anti-fibrinolytic agents; anti-fungal agents; anti-glaucoma agents; antihelminthics; anti-hemophilic agents; anti-hemophilic Factor; anti-hemorrhagic agents; antihistamines; anti-hyperlipidemic agents; anti-hyperlipoproteinemic agents; antihypertensive agents; anti-hypotensives; anti-infective agents such as antibiotics and antiviral agents; anti-inflammatory agents, both steroidal and non-steroidal; anti-keratinizing agents; anti-malarial agents; antimicrobial agents; anti-migraine agents; anti-mitotic agents; anti-mycotic agents; antinauseants; antineoplastic agents; anti-neutropenic agents; anti-obsessional agents; anti-parasitic agents; antiparkinsonism drugs; anti-pneumocystic agents; anti-proliferative agents; anti-prostatic hypertrophy drugs; anti-protozoal agents; antipruritics; anti-psoriatic agents; antipsychotics; antipyretics; anti spasmodics; anti-rheumatic agents; anti-schistosomal agents; anti-seborrheic agents; anti-spasmodic agents; anti-tartar and anti-calculus agents; anti-thrombotic agents; anti-tubercular agents; antitussive agents; anti-ulcerative agents; anti-urolithic agents; antiviral agents; GERD medications, anxiolytics; appetite suppressants; attention deficit disorder (ADD) and attention deficit hyperactivity disorder (ADHD) drugs; bacteriostatic and bactericidal agents; benign prostatic hyperplasia therapy agents; blood glucose regulators; bone resorption inhibitors; bronchodilators; carbonic anhydrase inhibitors; cardiovascular preparations including anti-anginal agents, anti-arrhythmic agents, beta-blockers, calcium channel blockers, cardiac depressants, cardiovascular agents, cardioprotectants, and cardiotonic agents; central nervous system (CNS) agents; central nervous system stimulants; choleretic agents; cholinergic agents; cholinergic agonists; cholinesterase deactivators; coccidiostat agents; cognition adjuvants and cognition enhancers; cough and cold preparations, including decongestants; depressants; diagnostic aids; diuretics; dopaminergic agents; ectoparasiticides; emetic agents; enzymes which inhibit the formation of plaque, calculus or dental caries; enzyme inhibitors; estrogens; fibrinolytic agents; fluoride anticavity/antidecay agents; free oxygen radical scavengers; gastrointestinal motility agents; genetic materials; glucocorticoids; gonad-stimulating principles; hair growth stimulants; hemostatic agents; herbal remedies; histamine H2 receptor antagonists; hormones; hormonolytics; hypnotics; hypocholesterolemic agents; hypoglycemic agents; hypolipidemic agents; hypotensive agents; HMGCoA reductase inhibitors; immunizing agents; immunomodulators; immunoregulators; immunostimulants; immunosuppressants; impotence therapy adjuncts; inhibitors; keratolytic agents; leukotriene inhibitors; LHRH agonists; liver disorder treatments; luteolysin agents; memory adjuvants; mental performance enhancers; metal chelators such as ethylenediaminetetraacetic acid, tetrasodium salt; mitotic inhibitors; mood regulators; mucolytics; mucosal protective agents; muscle relaxants; mydriatic agents; narcotic antagonists; nasal decongestants; neuroleptic agents; neuromuscular blocking agents; neuroprotective agents; nicotine; NMDA antagonists; non-hormonal sterol derivatives; nutritional agents, such as vitamins, essential amino acids and fatty acids; ophthalmic drugs such as antiglaucoma agents; oxytocic agents; pain relieving agents; parasympatholytics; peptide drugs; plasminogen activators; platelet activating factor antagonists; platelet aggregation inhibitors; post-stroke and post-head trauma treatments; potentiators; progestins; prostaglandins; prostate growth inhibitors; proteolytic enzymes as wound cleansing agents; prothyrotropin agents; psychostimulants; psychotropic agents; radioactive agents; regulators; relaxants; repartitioning agents; scabicides; sclerosing agents; sedatives; sedative-hypnotic agents; selective adenosine A1 antagonists; serotonin antagonists; serotonin inhibitors; serotonin receptor antagonists; steroids, including progestogens, estrogens, corticosteroids, androgens and anabolic agents; smoking cessation agents; stimulants; suppressants; sympathomimetics; synergists; thyroid hormones; thyroid inhibitors; thyromimetic agents; tranquilizers; tooth desensitizing agents; tooth whitening agents such as peroxides, metal chlorites, perborates, percarbonates, peroxyacids, and combinations thereof; unstable angina agents; uricosuric agents; vasoconstrictors; vasodilators including general coronary, peripheral and cerebral; vulnerary agents; wound healing agents; xanthine oxidase inhibitors; and the like.

Effective amount: The amount of an active agent (alone or with one or more other active agents) sufficient to induce a desired response, such as to prevent, treat, reduce and/or ameliorate a disease or a condition. Effective amounts of an active agent, alone or with one or more other active agents, can be determined in many different ways, such as assaying for a reduction in of one or more signs or symptoms associated with the disease or condition in the subject or measuring the level of one or more molecules associated with the condition to be treated.

Emulsifying Agents: Surfactants that reduce the interfacial tension between oil and water, minimizing the surface energy through formation of globules. Examples include, but are not limited to, glyceryl monostearate, methylcellulose, sodium lauryl sulfate, sodium oleate, sorbitan monopalmitate, sorbitan monostearate, sorbitan tristrearate, tragacanth, triethanolamine oleate, polyethylene sorbitan monolaurate, poloxamer, and any combination thereof.

Flow Cytometry: A technique that separates cells using their cell surface markers, thus identifying viable cells that can be grown in clonal cultures.

Homogeneous: One or more populations of cells in which more than 95%, of the cells are of the same phenotype, as determined by a pre-selected cell surface marker.

Huntington's Disease (HD): A fatal genetic disorder that causes the progressive breakdown of nerve cells in the brain and the deterioration of a person's physical and mental abilities. Every child of a parent with HD has a 50/50 chance of carrying the faulty gene. HD has no cure. Today, there are approximately 30,000 symptomatic Americans and more than 200,000 at-risk of inheriting the disease. Symptoms usually appear between the ages of 30 to 50, and worsen over a 10 to 25 year period. They include personality changes, mood swings, depression, forgetfulness, impaired judgment, unsteady gait, involuntary movements, slurred speech, difficulty in swallowing and significant weight loss.

Hydrogel: A water-swellable polymeric matrix that can absorb a substantial amount of water to form elastic gels. The matrix is a three-dimensional network of macromolecules held together by covalent or non-covalent crosslinks. Upon placement in an aqueous environment, dry hydrogels swell to the extent allowed by the degree of cross-linking.

Hydrogel Composition: A composition that either contains a hydrogel or is entirely composed of a hydrogel. Thus, "hydrogel compositions" encompass not only hydrogels per se but also compositions that comprise a hydrogel and one or more non-hydrogel components or compositions, e.g., hydrocolloids, which contain a hydrophilic component (which may contain or be a hydrogel) distributed in a hydrophobic phase.

Hydrophilic: A polymer, substance or compound that is capable of absorbing more than 10%/w of water at 100% relative humidity (rh).

Hydrophobic: A polymer, substance or compound that is capable of absorbing no more than 1%/w of water at 100% relative humidity (rh).

Hygroscopic: A polymer, substance or compound that is capable of absorbing more than 20 wt % of water at 100% relative humidity (rh).

Immune Response: The reaction to and interaction with substances interpreted by the body as not-self. The immune response depends on a functioning thymus and the conversion of stem cells to B and T lymphocytes. These lymphocytes contribute to antibody production, cellular immunity, and immunologic memory. Pathologic conditions associated with an abnormal immune response (immunopathy) may result from immuno-depression, excessive production of gamma globulins, overreaction to antigens of extrinsic origin, or abnormal response of the body to its own cells and tissues. Factors that may cause or contribute to suppression of the immune response include (1) congenital absence of the thymus or of the stem cells that are precursors of B and T lymphocytes; (2) malnutrition, in which there is a deficiency of the specific nutrients essential to the life of antibody-synthesizing cells; (3) cancer, viral infections, and extensive burns, all of which overburden the immune response mechanisms and rapidly deplete the supply of antigen-specific antibody; (4) certain drugs, including alcohol and heroin, some antibiotics, antipsychotics, and the antineoplastics used in the treatment of cancer. Overproduction of gamma globulins is manifested by an excessive proliferation of plasma cells (multiple myeloma). Hypersensitivity is the result of an overreaction to substances entering the body.

Inhibiting a condition: Reducing, slowing, or even stopping the development of a condition, for example, in a subject who is at risk of developing or has a particular condition.

Interferon-gamma: IFN-γ, or type II interferon, is a cytokine inducing macrophages and Class II major histocompatibility complex (MHC) molecule expression. Aberrant IFNγ expression is associated with a number of autoinflammatory and autoimmune diseases. IFNγ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops.

Interferon-type I: a large group of interferon proteins that bind to interferon receptors and regulate the activity of the immune system.

Keratolytic Agent: An agent that that thins or softens the skin. Exemplary keratolytic agents include urea, lactic acid, allantoin, benzoyl peroxide, salicyclic acid, sulfur, tretinoin, fluorouracil, trichloroacetic acid, and glycolic acid.

Lipophilic: A substance or compound that has an affinity for a non-polar environment compared to a polar or aqueous environment.

Localized application: The application of an active agent in a particular location in the body.

Marker: A nucleic acid or polypeptide that is differentially expressed in a cell of interest, such that the cell of interest can be identified and distinguished from other cells using any of a variety of methods known in the art. Exemplary markers found on stem cells include, but are not limited to, SSEA3, SSEA4, Tra-1-60, Tra-1-81, CD117 and CD90.

Monocytes: The largest type of leukocytes or white blood cells, which can differentiate into macrophages and myeloid lineage dendritic cells. Monocytes are produced by the bone marrow from monoblasts, which differentiate from hematopoietic stem cells. Monocytes circulate in the bloodstream for about one to three days and then typically move into tissues throughout the body where they differentiate into macrophages and dendritic cells. Monocytes and their macrophage and dendritic-cell progeny serve three main functions in the immune system: phagocytosis, antigen presentation, and cytokine production. Phagocytosis is the process of uptake of microbes and particles followed by digestion and destruction of this material. Monocytes are also capable of killing infected host cells via antibody-dependent cell-mediated cytotoxicity.

Mucosa: A membrane that lines various cavities in the body and covers the surface of internal organs. It consists of one or more layers of epithelial cells overlying a layer of loose connective tissue. The mucosa is mostly of endodermal origin and is continuous with the skin at various body openings such as the eyes, ears, inside the nose, inside the mouth, lip, vagina, the urethral opening and the anus. Some mucous membranes secrete mucus, a thick protective fluid. The function of the membrane is to stop pathogens and dirt from entering the body and to prevent bodily tissues from becoming dehydrated.

Mucosal Administration: Administration through the mouth, nose, vagina, eyes and ears of a subject.

Multiple sclerosis (MS): A progressive neurodegenerative disorder that involves an immune-mediated process in which the body's immune system is directed against myelin, a protective coating of nerve fibers in the CNS, the nerve fibers and the cells that produce myelin. The damage may produce a variety of neurological symptoms. The cause of MS is not known, and there is no cure for MS.

Multiple System Atrophy (MSA): A rare, degenerative neurologic condition that affects both men and women, usually starting in the 50's or early 60's. Similar to Parkinson's disease, MSA affects cells that produce dopamine, a neurotransmitter that controls motor commands. In addition, MSA affects both neurons and glial cells.

Nanog: A homeodomain-containing transcription factor essential for maintenance of pluripotency and self-renewal in embryonic stem cells. Expression is controlled by a network of factors including Sox2 and the key pluripotency regulator Oct-4.

Neonatal Encephalopathy: A neonatal ischemic brain injury, which causes permanent motor-deficit cerebral palsy and may result in death.

Neurodegenerative Disease: An acute or chronic condition, disorder or disease of the central or peripheral nervous system. A neurodegenerative condition may be age-related, or it may result from injury or trauma, or it may be related to a specific disease or disorder. Acute neurodegenerative conditions include, but are not limited to, conditions associated with neuronal cell death or compromise, including cerebrovascular insufficiency, focal or diffuse brain trauma, diffuse brain damage, spinal cord injury or peripheral nerve trauma. Examples of acute neurodegenerative disorders include, but are not limited to, cerebral ischemia, infarction, embolic occlusion, thrombotic occlusion, reperfusion following acute ischemia, perinatal hypoxic-ischemic injury, cardiac arrest, intracranial hemorrhage, intracranial and intravertebral lesions, whiplash and shaken infant syndrome. Chronic neurodegenerative conditions include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia), demyelination diseases and disorders including multiple sclerosis and hereditary diseases such as leukodystrophies.

Neuron: An electrically excitable cell that receives, processes, and transmits information through electrical and chemical signals via specialized connections called synapses. Neurons are the primary components of the central nervous system, which includes the brain and spinal cord, and of the peripheral nervous system, which comprises the autonomic nervous system and the somatic nervous system. Sensory neurons respond to touch, sound, or light and convert the stimulus into an electrical signal via transduction, which is then sent to the spinal cord or brain. Motor neurons receive signals from the brain and spinal cord to control muscle contractions and glandular output. Interneurons connect neurons to other neurons within the same region of the brain or spinal cord in neural networks. A typical neuron consists of a cell body (soma), dendrites, and an axon. Dendrites are thin structures that arise from the cell body, often extending for hundreds of micrometers and branching multiple times, giving rise to a complex "dendritic tree". Axons are special cellular extensions that travel for a distance. Numerous axons are often bundled into fascicles that make up the nerves in the peripheral nervous system. Neurons are generated by stem cells during brain development and childhood. Neurons in the adult brain generally do not undergo cell division. Astrocytes are star-shaped glial cells, which are non-neuronal cells that maintain homeostasis, form myelin, and provide support and protection for neurons in the central and peripheral nervous systems.

Nutraceutical: A pharmaceutical-grade and standardized nutrient, dietary supplement or food additive.

Oil: Any fatty substance that is in liquid form at room temperature (25° C.) and at atmospheric pressure (760 mmHg). An oily phase in a pharmaceutical composition may comprise at least one polar or apolar hydrocarbon-based oil.

Oral: oral administration includes food, beverages, drinks, soups, baked goods, syrups, oral pharmaceutical compositions, nutraceutical formulations, and the like. Liquid dosage forms for oral administration include, but are not limited to, pharmaceutically acceptable emulsions, solutions, suspensions, syrups and elixirs.

OCT-4 (Octamer-Binding Transcription Factor 4): A transcription factor expressed in undifferentiated pluripotent embryonic stem cells and germ cells during normal development. Together with Sox2 and Nanog, it is necessary for the maintenance of pluripotent potential.

Parenteral: A type of administration that includes subcutaneous injections, intravenous, intramuscular, intrasternal injection or infusion techniques. Compositions for parenteral injection comprise pharmaceutically acceptable sterile aqueous or nonaqueous solutions, dispersions, suspensions or emulsions as well as sterile powders for reconstitution into sterile injectable solutions or dispersions prior to use.

Parkinson's Disease (PD): A brain disorder that leads to shaking, stiffness, difficulty with walking, balance, and coordination, mental and behavioral changes, sleep problems, depression, memory difficulties, and fatigue. Parkinson's symptoms usually begin gradually and get worse over time. The disease affects about 50 percent more men than women, and its typical onset occurs at about age 60. PD is triggered when neurons in the brain die, with consequent reduction in the production of dopamine and norepinephrine. The lack of dopamine causes the movement problems associated with PD, and the loss of norepinephrine leads to fatigue, irregular blood pressure, decreased movement of food through the digestive tract, and sudden drop in blood pressure when a person stands up from a sitting or lying-down position. Symptoms of PD include, but are not limited to, tremor in hands, arms, legs, jaw, or head; stiffness of the limbs and trunk; slowness of movement; impaired balance and coordination; depression; difficulty swallowing, chewing, and speaking; urinary incontinence or constipation, skin problems; and sleep disruptions. The main therapy for Parkinson's is levodopa to produce dopamine, in combination with carbidopa to prevent or reduce some of the side effects of levodopa. Once this therapy is no longer effective, subjects with PD are treated with dopamine agonists, MAO-B inhibitors, COMT inhibitors, Amantadine, and/or anticholinergic drugs to slow progression of the disease. There are currently no blood or laboratory tests to diagnose non-genetic cases of Parkinson's disease and there is no cure for Parkinson's disease.

Periventricular Leukomalacia: A type of brain injury that affects premature infants. The condition involves the death of small areas of brain tissue around the ventricles.

Permeation Enhancer: A natural or synthetic molecule that facilitates the transport of co-administered active agents across biological membranes.

pH Modifier: A molecule or buffer used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate), and pharmaceutically acceptable salts thereof.

Pharmaceutically acceptable carriers: The pharmaceutically acceptable carriers useful in this disclosure are conventional. Remington's Pharmaceutical Sciences, by E. W. Martin, Mack Publishing Co., Easton, PA, 19th Edition (1995), describes compositions and formulations suitable for pharmaceutical delivery of the compositions herein disclosed. The nature of the carrier can depend on the particular mode of administration being employed. For instance, oral applications usually include pharmaceutically and physiologically acceptable fluids such as water, physiological saline, balanced salt solutions, aqueous dextrose, glycerol or the like as a vehicle. In addition to biologically-neutral carriers, oral compositions may also contain minor amounts of non-toxic auxiliary substances, such as wetting or emulsifying agents, preservatives, and pH buffering agents and the like.

Plasticizer: A material that, when added to a polymer, imparts an increase in flexibility, workability, and other properties to the finished product. Exemplary plasticizers include, but are not limited to, glycerol, sorbitol, polyethylene glycol, polypropylene glycol, polyethylene-propylene glycol, and any combination thereof.

Polymer: Includes homopolymers, linear and branched polymer structures, crosslinked polymers, copolymers (which may or may not be crosslinked), block copolymers, alternating copolymers, random copolymers, and the like. Oligomers are polymers having a molecular weight below about 1000 Da.

Proinflammatory Cytokines: cytokines produced predominantly by activated macrophages and involved in the upregulation of inflammatory reactions. Exemplary proinflammatory cytokines include, but are not limited to, IL-1β, IL-6, and TNF-α. IL-1β is released primarily by monocytes and macrophages during cell injury, infection, invasion, and inflammation. IL-1β expression is enhanced following crush injury to peripheral nerve and after trauma in microglia and astrocytes in the central nervous system (CNS), and can produce hyperalgesia following either intraperitoneal, intracerebroventricular or intraplantar injection. IL-6 plays a role in the neuronal reaction to nerve injury, and contributes to the development of neuropathic pain behavior following a peripheral nerve injury. TNF-α, also known as cachectin, is an inflammatory cytokine that acts on several different signaling pathways through two cell surface receptors, TNFR1 and TNFR2, to regulate apoptotic pathways, NF-kB activation of inflammation, and activate stress-activated protein kinases (SAPKs).

Radiation therapy: A use of directed gamma rays or beta rays to induce sufficient damage to a cell so as to limit its ability to function normally or to destroy the cell altogether.

Scaffold: A structural support for stem cell adhesion, proliferation and differentiation, which also serves as a microenvironment for guiding stem cell differentiation and tissue regeneration and for controlling tissue structure. Natural scaffolds used in tissue engineering include, but are not limited to, collagen, silk fibroin, alginate, chitosan, keratin, and decellularized tissues such as de-epithelialized human amniotic membrane. Synthetic scaffolds are usually made of biodegradable polymers. Biocompatible scaffolds are precursors to implantable devices, which have the ability to perform an intended function, without eliciting any undesirable effect in the stem cells or inducing any undesirable local or systemic responses in the eventual host.

Skeleton: A supporting structure of an organism. The endoskeleton is the internal support structure of an animal, it is composed of mineralized tissue and is typical of vertebrates. Endoskeletons, the internal support structure inside the body, vary in complexity from functioning purely for support, as in sponges, to serving as an attachment site for muscles and a mechanism for transmitting muscular forces. A true endoskeleton is derived from mesodermal tissue. In most vertebrates, the main components of the skeleton are bones and cartilage, which in mammals is found mainly in the joint areas.

Skin: The largest organ in the body consisting of several layers. The skin plays an important role in biologic homeostasis, and is comprised of the epidermis and the dermis. The epidermis, which is composed of several layers beginning with the stratum corneum, is the outermost layer of the skin, and the deep dermis is the innermost skin layer. The skin has multiple functions, including thermal regulation, metabolic function (vitamin D metabolism), and immune functions. In humans, the usual thickness of the skin is 1-2 mm, although in some areas the skin may be more than 5 mm thick. The epidermis provides the body's buffer zone against the environment and protection from trauma, excludes toxins and microbial organisms, and constitutes a semi-permeable membrane. The stratum corneum is an avascular, multilayer structure that functions as a barrier to the environment and prevents trans-epidermal water loss. Below the stratum corneum are the stratum lucidum, stratum granulosum, stratum germinativum, and stratum basale, each containing living cells with specialized functions. Dermal appendages, which include hair follicles, sebaceous and sweat glands, fingernails, and toenails, originate in the epidermis and protrude into the dermis hair follicles. The sebaceous glands are responsible for secretions that lubricate the skin, and sweat gland secretions control skin pH to prevent dermal infections. The sweat glands, dermal blood vessels, and small muscles control temperature on the surface of the body. Nerve endings in the skin include receptors for pain, touch, heat, and cold. The basement membrane separates and connects the epidermis and dermis. The dermis is a vascular structure that supports and nourishes the epidermis. In addition, there are sensory nerve endings in the dermis that transmit signals regarding pain, pressure, heat, and cold. The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin, which give the skin its turgor. Fibronectin and hyaluronic acid are secreted by the fibroblasts. The deep dermis is located over the subcutaneous fat; it contains larger networks of blood vessels and collagen fibers to provide tensile strength. It also consists of fibroelastic connective tissue, which is composed mainly of collagen.

Skin Simulating Membrane: A semi-permeable membrane used to replicate the skin in diffusion testing.

Stem Cells: Undifferentiated cells capable of prolonged self-replication without differentiation, and characterized by the presence of surface markers associated with self-renewal without differentiation. Sytem cells may also be characterized by the presence of transcription factors associated with pluripotency. Stem cells are also characterized by their ability to differentiate in vitro into functional cells of various cell lineages from multiple germ layers (endoderm, mesoderm and ectoderm). Stem cells give rise to tissues of multiple germ layers following transplantation. Based on their developmental potential, stem cells are classified as: totipotent stem cells, which have the potential to differentiate into lineages from mesodermal, ectodermal and endodermal tissues, such as osteogenic, neurogenic and hepatic lineages; pluripotent stem cells, which have to potential to differentiate into various embryonic cell types; multipotent stem cells, which have the potential to differentiate into cell lineages all within a particular tissue, organ, or physiological system; oligopotent stem cells, which have the potential to differentiate into a few cell lineages; and unipotent stem cells, which have the potential to differentiate into a single cell lineage. Differentiation is the process by which an undifferentiated cell differentiates into a specialized cell such as, for example, a nerve cell, a bone cell or a muscle cell. The lineage of a cell defines which cells the cell came from and what cells it can give rise to.

SOX-2 or SRY (sex determining region Y)-box 2: A transcription factor expressed in undifferentiated pluripotent embryonic stem cells and germ cells during development. Together with Oct-4 and Nanog, it is necessary for the maintenance of pluripotent potential.

SSEA4: Stage-specific embryonic antigen-4 is a glycolipid carbohydrate expressed on the surface of human teratocarcinoma stem, embryonic germ, and embryonic stem cells. Expression of human SSEA4 decreases following differentiation of human embryonic carcinoma cells, but increases following differentiation in mouse cells.

Subject: A living multi-cellular vertebrate organism, a category that includes human and non-human mammals, as well as birds (such as chickens and turkeys), fish, and reptiles. Exemplary subjects include mammals, such as human and non-human primates, rats, mice, dogs, cats, rabbits, cows, pigs, goats, horses, and the like.

Surface or Body Surface: A surface located on the human body or within a body orifice. Thus, a "body surface" includes, by way of example, skin, teeth, skin or mucosal tissue, including the interior surface of body cavities that have a mucosal lining.

Teratogen: An agent able to disturb the development of an embryo or fetus, by halting pregnancy or by producing a congenital malformation, such as a birth defect. Teratogens include, but are not limited to, radiation, maternal infections, chemicals, toxic agents and drugs.

Topical administration: Delivery of an active agent to a body surface, such as, the skin or mucosa, as in, for example, topical drug administration in the prevention or treatment of various skin disorders.

Toxic agent: An agent or substance that can produce an adverse biological effect. A toxic agent may be chemical, physical, or biological in nature. Toxic agents include, but are not limited to, inorganic substances such as lead, mercury, hydrofluoric acid, cyanide, and chlorine gas, organic compounds such as alcohol, radiations, coal dust, asbestos fibers, finely divided silicon dioxide, plant and pathogen toxins, snake venom, lithium and abused substances, such as marijuana and cocaine.

TRA-1-60: A >200 kDa pluripotent stem cell-specific protein expressed on the surface of undifferentiated human embryonic stem (ES) and induced pluripotent stem (iPS) cells, embryonal carcinoma (EC) cells and embryonic germ (EG) cells, as well as rhesus monkey ES cell lines. A soluble form of TRA-1-60 has been detected in serum of patients with embryonal carcinoma. The epitope, which is lost upon cell differentiation, contains sialic acid and is associated with a large-molecular-mass transmembrane protein named podocalyxin.

Transdermal: A route of administration by which active ingredients are delivered across the skin for systemic distribution. Examples include transdermal patches for drug delivery.

Under conditions sufficient to: A phrase that is used to describe any environment that permits the desired activity.

Vitamin: An organic molecule and essential micronutrient, which an organism needs in small quantities for the proper functioning of its metabolism. The thirteen vitamins required by human metabolism are: vitamin A (retinols and carotenoids), vitamin $B_1$ (thiamine), vitamin $B_2$ (riboflavin), vitamin $B_3$ (niacin), vitamin $B_5$ (pantothenic acid), vitamin $B_6$ (pyridoxine), vitamin $B_7$ (biotin), vitamin $B_9$ (folic acid or folate), vitamin $B_{12}$ (cobalamins), vitamin C (ascorbic acid), vitamin D (calciferols), vitamin E (tocopherols and tocotrienols), and vitamin K (quinones). Vitamins have diverse biochemical functions. Some forms of vitamin A function as regulators of cell and tissue growth and differentiation. The B complex vitamins function as enzyme cofactors or precursors. Vitamin D functions as a regulator of mineral metabolism for bones and other organs. Vitamins C and E function as antioxidants. Both deficient and excess intake of a vitamin can potentially cause clinically significant illness.

Water-Insoluble: A polymer, compound or composition with a solubility in water of less than 5%/w, less than 3%/w, or less than 1%/w, as measured in water at 20° C.

Water-Swellable: A polymer, substance or compound, that may absorb an amount of water greater than at least 25%/w of its own weight, or greater than at least 50%/w, upon immersion in an aqueous medium.

Homogeneous Human Amniotic Fluid Clonal Stem Cell Lines

The use of drugs, nutritional agents and toxic substances by pregnant women may have major effects on the developing fetus. However, ethical considerations prevent most clinical studies in pregnant women, and the study of drug effects on human fetuses has been limited to measurements in maternal and umbilical cord blood and neonatal assessments. Therefore, nearly all of the information is based on animal studies. Only in vitro studies on placental tissue or placental perfusion have been used in humans. There is a need for a reliable test that uses human fetal cells to directly assess the effects of drugs, nutritional agents and toxic substances on fetal tissues and on human fetal growth and development.

Stem cells are undifferentiated cells capable of self-renewal and differentiation. Bone marrow, peripheral blood, umbilical cord cells, embryonic tissue and umbilical cord blood cells are all potential sources of stem cells. However, the use of these cells is limited by their cell number, survival in culture, ability to proliferate and potential tumorigenesis. Moreover, ethical considerations have restricted the collection of embryonic and umbilical cord blood cells.

Amniotic fluid cells are a potential source of stem cells for clinical purposes and present the advantage of being free from ethical concerns, as an abundant supply of amniotic fluid cells may be easily obtained when performing amniocentesis, a standard procedure for genetic testing. In addition, they remain viable, proliferate rapidly even after numerous passages, they are not tumorigenic and are multipotent, with the potential for expansion in vitro to multiple cell lines. A major limiting factor with the use of amniotic fluid cells is their extensive individual variations or heterogeneity, which makes it necessary to use multiple samples from different individuals to perform laboratory research. There are currently no standard assays to assess changes in human fetus cell growth and differentiation in response to exposure to drugs or toxic agents.

The present inventors have unexpectedly and surprisingly developed unique homogeneous clones of human amniotic fluid stem cells that have a normal karyotype, do not form tumors in a host, are capable of self-renewal, and are capable of differentiation to cells of endodermal, ectodermal and mesodermal lineages.

The disclosed homogeneous human amniotic fluid clonal stem cell lines consistently express the stem cell surface markers CD90, SSEA4 and TRA-1-60, and the embryonic transcription factors associated with pluripotency OCT4, Nanog, SOX-2, REX-1, CD117, CD15, CD44, CD29, CD9, CD73 AND CD133. In particular, 95% to 99% of the homogeneous amniotic fluid stem cells consistently express CD90, 27% of the homogeneous amniotic fluid stem cells consistently express SSEA4 and 5-10% of the homogeneous amniotic fluid stem cells consistently express TRA-1-60 after five passages or more.

Also provided herein are pharmaceutical compositions that comprise the disclosed homogeneous human amniotic fluid clonal stem cell lines. In some embodiments, the pharmaceutical composition may comprise one or more of a pharmaceutically acceptable excipient, a pharmaceutically acceptable carrier, a diluent, adjuvant, stabilizer, emulsifier, preservative, colorant, or buffer. In some embodiments, the pharmaceutical composition may additionally comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an antibacterial agent or an antifungal agent.

Bioassays and Methods for Pharmaceutical Testing

The present inventors have developed homogeneous human amniotic fluid stem cell bioassays to determine the effects of drugs, nutraceuticals, and toxic agents on human fetus growth, survival and differentiation, as wells as methods that make use of the disclosed bioassays. The bioassays provided herein comprise cell cultures of one or more homogeneous human amniotic fluid clonal stem cell lines. In some embodiments, the bioassays may include dose-responsive reporter genes driven by inducible promoters, or labeling antibodies.

The disclosed bioassays and methods present remarkable advantages over current approaches, as they employ human cells rather than animal models, and fetal cells rather than placental or cord blood cells, thus allowing examination of effects on fetal tissue differentiation in addition to effects on fetus growth and survival.

The disclosed methods for screening agents for their effects on a human fetus comprise: (1) culturing bioassay samples and incubating the samples (a) in absence of the agent; (b) after a short, single exposure to the agent; or (c) in continuous presence of the agent, to produce three-dimensional spherical colonies of the disclosed homogeneous human amniotic fluid clonal stem cell lines; (2) determining the agent's effect on each sample by assessing changes in growth, proliferation or differentiation of the homogeneous human amniotic fluid clonal stem cells brought about by the agent; and (3) if an effect is detected, quantifying the agent's effect by dose effect and/or gene expression.

In some embodiments, the agent is a drug, a compound, a vitamin, an omega-3 fatty acid, a supplement, a food additive, a toxic agent, or a potential teratogen. Toxic agents may include, but are not limited to, an opioid, lithium, marijuana, cocaine or a radiation. Potential teratogens may include, but are not limited to, an ACE inhibitor, a blood thinner, a hormone, an anti-depressant, a seizure medication, an anti-rheumatic agent, streptomycin, valproic acid, or thalidomide.

Drugs may include, but are not limited to, one or more of adrenergic agents; adrenocortical steroids; adrenocortical suppressants; alcohol deterrents; aldosterone antagonists; amino acids; ammonia detoxicants; anabolic agents; analeptic agents; analgesic agents; androgenic agents; anesthetic agents; anorectic compounds; anorexic agents; antagonists; anterior pituitary activators and anterior pituitary suppressants; anti-acne agents; anti-adrenergic agents; anti-allergic agents; anti-amebic agents; anti-androgen agents; anti-anemic agents; anti-anginal agents; anti-anxiety agents; anti-arthritic agents; anti-asthmatic agents; anti-atherosclerotic agents; anti-bacterial agents; anti-cancer agents; anticholinergics; anticholelithogenic agents; anti-coagulants; anti-coccidal agents; anti-convulsants; anti-depressants; anti-diabetic agents; anti-diarrheals; anti-diuretics; antidotes; anti-dyskinetics agents; anti-emetic agents; anti-epileptic agents; anti-estrogen agents; anti-fibrinolytic agents; anti-fungal agents; anti-glaucoma agents; antihelminthics; anti-hemophilic agents; anti-hemophilic Factor; anti-hemorrhagic agents; antihistamines; anti-hyperlipidemic agents; anti-hyperlipoproteinemic agents; antihypertensive agents; anti-hypotensives; anti-infective agents; anti-inflammatory agents; anti-keratinizing agents; anti-malarial agents; anti-microbial agents; anti-migraine agents; anti-mitotic agents; anti-mycotic agents; antinauseants; antineoplastic agents; anti-neutropenic agents; anti-obsessional agents; anti-parasitic agents; antiparkinsonism drugs; anti-pneumocystic agents; anti-proliferative agents; anti-prostatic hypertrophy drugs; anti-protozoal agents; antipruritics; anti-psoriatic agents; antipsychotics; antipyretics; antispasmodics; anti-rheumatic agents; anti-schistosomal agents; anti-seborrheic agents; anti-spasmodic agents; anti-tartar and anti-calculus agents; anti-thrombotic agents; anti-tubercular agents; antitussive agents; anti-ulcerative agents; anti-urolithic agents; antiviral agents; GERD medications, anxiolytics; appetite suppressants; attention deficit disorder (ADD) and attention deficit hyperactivity disorder (ADHD) drugs; bacteriostatic and bactericidal agents; benign prostatic hyperplasia therapy agents; blood glucose regulators; bone resorption inhibitors; bronchodilators; carbonic anhydrase inhibitors; cardiovascular preparations including anti-anginal agents, anti-arrhythmic agents, beta-blockers, calcium channel blockers, cardiac depressants, cardiovascular agents, cardioprotectants, and cardiotonic agents; central nervous system (CNS) agents; central nervous system stimulants; choleretic agents; cholinergic agents; cholinergic agonists; cholinesterase deactivators; coccidiostat agents; cognition adjuvants and cognition enhancers; cough and cold preparations, including decongestants; depressants; diagnostic aids; diuretics; dopaminergic agents; ectoparasiticides; emetic agents; enzymes; enzyme inhibitors; estrogens; fibrinolytic agents; fluoride anticavity/antidecay agents; food additives; free oxygen radical scavengers; gastrointestinal motility agents; genetic materials; glucocorticoids; gonad-stimulating principles; hair growth stimulants; hemostatic agents; herbal remedies; histamine H2 receptor antagonists; hormones; hormonolytics; hypnotics; hypocholesterolemic agents; hypoglycemic agents; hypolipidemic agents; hypotensive agents; HMGCoA reductase inhibitors; immunizing agents; immunomodulators; immunoregulators; immunostimulants; immunosuppressants; impotence therapy adjuncts; inhibitors; keratolytic agents; leukotriene inhibitors; LHRH agonists; liver disorder treatments; luteolysin agents; memory adjuvants; mental performance enhancers; metal chelators such as ethylenediaminetetraacetic acid, tetrasodium salt; mitotic inhibitors; mood regulators; mucolytics; mucosal protective agents; muscle relaxants; mydriatic agents; narcotic antagonists; nasal decongestants; neuroleptic agents; neuromuscular blocking agents; neuroprotective agents; nicotine; NMDA antagonists; non-hormonal sterol derivatives; nutritional agents; vitamins; essential amino acids; essential fatty acids; antiglaucoma agents; oxytocic agents; pain relieving agents; parasympatholytics; peptide drugs; plasminogen activators; platelet activating factor antagonists; platelet aggregation inhibitors; post-stroke and post-head trauma treatments; potentiators; progestins; prostaglandins; prostate growth inhibitors; proteolytic enzymes; prothyrotropin agents; psychostimulants; psychotropic agents; radioactive agents; regulators; relaxants; repartitioning agents; scabicides; sclerosing agents; sedatives; sedative-hypnotic agents; selective adenosine A1 antagonists; serotonin antagonists; serotonin inhibitors; serotonin receptor antagonists; steroids; smoking cessation agents; stimulants; suppressants; sympathomimetics; synergists; thyroid hormones; thyroid inhibitors; thyromimetic agents; tranquilizers; tooth desensitizing agents; tooth whitening agents; unstable angina agents; uricosuric agents; vasoconstrictors; vasodilators; vulnerary agents; wound healing agents; xanthine oxidase inhibitors; marijuana and cocaine.

Changes in growth, proliferation or differentiation of the homogeneous human amniotic fluid clonal stem cells brought about by exogenous agents may be determined and quantified by routine techniques known in the art. Exemplary techniques include, but are not limited to, fluorescence microscopy, enzymatic colorimetric assays, flow cytometry, monoclonal antibody binding, differential gene expression analysis, and genomic analysis.

Thus, the homogeneous human amniotic fluid clonal stem cell bioassays and methods disclosed herein provide a highly effective and useful model for the screening of active agents and the detection and assessment of their potentially hazardous effects on fetus growth, survival and differentiation.

Pharmaceutical Compositions and Scaffolds Comprising Homogeneous Human Amniotic Fluid Clonal Stem Cells Also provided herein are pharmaceutical compositions that comprise one or more clones of homogeneous human amniotic fluid clonal stem cells, for the prevention, management, control, correction or treatment of congenital malformations of a fetus, as well as for the management, control, correction or treatment of diseases associated with damaged tissues or dysfunctional organs in human subjects.

The disclosed pharmaceutical compositions may be administered to a fetus for the prevention, management, control, correction of a congenital malformation, or to an animal or human subject to treat a disease. The disclosed pharmaceutical compositions may be formulated for topical, parenteral, intravenous, intramucosal, muscular, stransdermal or intramuscular administration.

The pharmaceutical compositions may comprise pharmaceutically acceptable sterile aqueous or nonaqueous solutions, dispersions, suspensions or emulsions as well as sterile powders for reconstitution into sterile injectable solutions or dispersions prior to use. Examples of suitable aqueous and nonaqueous carriers, diluents, solvents or vehicles include, but are not limited to, water, ethanol, polyols, such as glycerol, propylene glycol, polyethylene glycol, and the like, carboxymethylcellulose and suitable mixtures thereof, vegetable oils, such as olive oil, and injectable organic esters, such as ethyl oleate. Proper fluidity can be maintained, for example, by the use of coating materials such as lecithin, by the maintenance of the required particle size in the case of dispersions, and by the use of surfactants. The disclosed pharmaceutical compositions may also contain adjuvants such as, but not limited to, preservatives, wetting agents, emulsifying agents, and dispersing agents, isotonic agents, such as sugars, sodium chloride, and the like, and agents that delay absorption, such as aluminum monostearate and gelatin.

Injectable depot forms may be made by forming microcapsule matrices of the disclosed homogeneous human amniotic fluid clonal stem cells in biodegradable polymers, such as polylactide-polyglycolide, poly(orthoesters) and poly(anhydrides). Depot injectable formulations may also be prepared by entrapping the disclosed homogeneous human amniotic fluid clonal stem cells in liposomes or microemulsions compatible with body tissues. Injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Prevention and/or treatment of infections can be achieved by the inclusion of antibiotics, as well as various antibacterial and antifungal agents, for example, paraben, chlorobutanol, phenol sorbic acid, and the like, in the disclosed pharmaceutical compositions.

The disclosed pharmaceutical compositions may contain one or more pharmaceutically acceptable excipients, diluents, adjuvants, stabilizers, emulsifiers, preservatives, colorants, buffers, flavor-imparting agents, bacteriostats, fungistats, emollients, plasticizers, permeation enhancers, antioxidants, pigments, lubricants, preservatives, wetting agents, salts, and any mixture thereof, and pharmaceutically acceptable carriers suitable for inhaled, parenteral, intravenous, topical, transdermal, mucosal, sub-mucosal, muscular, sub-muscular or intramuscular administration.

The disclosed pharmaceutical compositions may further comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

The pharmaceutical compositions provided herein, when administered to a subject, may treat, control, manage or prevent diseases associated with damaged tissues or dysfunctional organs, or cancer. The subject may be an animal or a human subject.

The disclosed homogeneous human amniotic fluid clonal stem cells have a broad array of additional uses. Uses include, but are not limited to, the manufacture of engineered tissue and organs, including structures such as scaffolds, patches or plugs of tissues or matrix material, prosthetics, and other implants, tissue scaffolding, repair or dressing of wounds, hemostatic devices, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, and fetuses.

In some examples the shape of the composition helps send signals to the cells to grow and reproduce in a specific type of desired way. Other substances, for example differentiation inducers, can be added to the compositions to promote specific types of cell growth. The ability to use the disclosed homogeneous human amniotic fluid clonal stem cells to bioengineer tissue or organs creates a wide variety of bioengineered tissue replacement applications. Examples of bioengineered components include, but are not limited to, bone, dental structures, joints, cartilage, skeletal muscle, smooth muscle, cardiac muscle, tendons, knees, menisci, ligaments, blood vessels, stents, heart valves, corneas, ear drums, nerve guides, tissue or organ patches or sealants, a filler for missing tissues, sheets for cosmetic repairs, skin, soft tissue structures of the throat such as trachea, epiglottis, and vocal cords, other cartilaginous structures such as nasal cartilage, tarsal plates, tracheal rings, thyroid cartilage, and arytenoid cartilage, connective tissue, vascular grafts and components thereof, and sheets for topical applications, and repair to or replacement of organs such as livers, kidneys, lungs and pancreas. In some examples, the disclosed homogeneous human amniotic fluid clonal stem cells may be combined with drugs to improve transplantation. For example, antibiotics, anti-inflammatory agents, local anesthetics, immunosuppressive agents, or combinations thereof, may be added to the matrix of a bioengineered organ to speed the healing process and reduce pain and discomfort. In some examples, the disclosed scaffolds may further comprise one or more biological agents. The biological agents may provide the biodegradable scaffolds with mechanical strength and control over their mechanical and degradation properties. Exemplary biological agents include, but are not limited to, fibronectin, collagen and gelatin, and synthetic polymers, such as a flexible nanofiber, polyethylene glycol or a polylactic glycolide.

The disclosed homogeneous human amniotic fluid clonal stem cells may also be banked and proliferated in culture as needed, as a convenient and readily available source for autologous therapies in histocompatible HLA type-matched recipients. Recipients can be animal or human subjects, or animal or human fetuses.

Tissue Engineering and Regenerative Medicine

Unlike any other amniotic fluid-derived stem cells known in the art, the disclosed human amniotic fluid clonal stem cells are homogeneous and identical in their phenotypic characteristics. The disclosed homogeneous human amniotic fluid clonal stem cells can be easily characterized, because 99-100% of the cells consistently express CD90, 27% of the cells consistently express SSEA4, and 5-10% of the cells consistently express TRA-1-60, even after numerous passages. The disclosed homogeneous clones display high self-renewal capacity and plasticity, and can be rapidly expanded while maintaining a stable karyotype and an undifferentiated phenotype, as they consistently express the pluripotency stem cell markers Oct-4, Sox-2, Nanog, Rex-1, CD117, CD15, CD44, CD29, CD9, CD73 and CD133.

The disclosed human amniotic fluid clonal stem cells have the ability to integrate into and regenerate damaged tissue thanks to their multi-lineage differentiation capacity. Moreover, the disclosed human amniotic fluid clonal stem cells have the ability to attach and proliferate on biodegradable scaffolds, and can be used for surgical implantation both in utero and after birth. Therefore, the disclosed human amniotic fluid clonal stem cells are ideal to treat or correct congenital malformations of the fetus, as well as diseases associated with damaged tissues or dysfunctional organs in human subjects.

Provided herein are methods of repairing a tissue or replacing an organ in subjects in need thereof. These methods comprise administering to the subject a pharmaceutical composition comprising one or more homogeneous human amniotic fluid clonal stem cell lines, thereby repairing the tissue or replacing the organ. Exemplary tissues or organs that can be repaired include, but are not limited to, a subject's respiratory tract, gastrointestinal tract, salivary glands, cardiovascular system, liver, pancreas, bone marrow, joints, bones, cartilage, muscles, knee, skeleton, central nervous system or skin. Administration includes, but is not limited to, topical, transdermal, mucosal, sub-mucosal, parenteral, intramuscular, sub-muscular, inhaled, parenteral, or intravenous administration.

The pharmaceutical compositions may contain one or more of a pharmaceutically acceptable excipient, diluent, adjuvant, stabilizer, emulsifier, preservative, colorant, buffer, or a pharmaceutically acceptable carrier suitable for topical, transdermal, mucosal, sub-mucosal, parenteral, intramuscular, sub-muscular, inhaled, parenteral, or intravenous administration. Moreover, the pharmaceutical compositions may be administered with, or may further comprise one or more of a cytokine, a growth factor, a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

The present inventors have also developed a method of treating a congenital malformation in a subject in need thereof. The method comprises (1) seeding one or more homogeneous human amniotic fluid clonal stem cell lines on a biodegradable scaffold; (2) inducing differentiation of the homogeneous human amniotic fluid clonal stem cell line on the biodegradable scaffold; and (3) treating the congenital malformation by transplanting the biodegradable scaffold into the subject.

The congenital malformation may be a genetic disorder, a tumor, an arrest of an organ development, or a result from exposure to a toxin, smoke, alcohol or fetal injury during pregnancy. Transplantation can be in utero or after birth.

In some examples, the congenital malformation is a bone or cartilage defect, and the disclosed homogeneous human amniotic fluid clonal stem cells differentiate into osteoblasts or osteocytes in an osteogenic medium.

In some examples, the congenital malformation is a heart tissue malformation, and the disclosed homogeneous human amniotic fluid clonal stem cells differentiate into myofibroblast and endothelial cells in a myogenic medium.

In some examples, the congenital malformation is a kidney malformation, and the disclosed homogeneous human amniotic fluid clonal stem cells differentiate into renal cells in a nephrogenic medium.

In some examples, the congenital malformation is a lung defect, and the disclosed homogeneous human amniotic fluid clonal stem cells differentiate into epithelial and mesenchymal cells in an alveolargenic medium.

In some other examples, the congenital malformation is a heart defect, and the disclosed homogeneous human amniotic fluid clonal stem cells differentiate into myocardial cells in a myogenic medium.

In some examples, the congenital malformation is periventricular leukomalacia, and the disclosed homogeneous human amniotic fluid clonal stem cells differentiate into angiogenic cells in an angiogenic medium.

In some examples, the congenital malformation is neonatal encephalopathy, and the disclosed homogeneous human amniotic fluid clonal stem cells differentiate into angiogenic cells in an angiogenic medium.

In some examples, the congenital malformation is traumatic brain injury, and the disclosed homogeneous human amniotic fluid clonal stem cells differentiate into neurons in a neurogenic medium.

In some examples, the disclosed methods may further comprise administering to the subject prior to, during or after transplantation one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

The disclosed homogeneous human amniotic fluid clonal stem cells, once administered to a subject, are capable of migrating to the site of injury and regenerating damaged tissues and organs, and thus can treat diseases associated traumatic injuries and dysfunctional tissues and organs.

Provided herein are methods of treating diseases associated with traumatic injuries and dysfunctional tissues and organs in subjects in need thereof, comprising administering the disclosed homogeneous human amniotic fluid clonal stem cells.

In some embodiments, provided herein are methods of repairing a tissue or replacing an organ in a subject in need thereof, wherein the methods comprise administering to the subject a pharmaceutical composition that comprises the disclosed homogeneous human amniotic fluid clonal stem cell lines to regenerate the tissue or organ, thereby repairing the tissue or replacing the organ in the subject. In some embodiments, the tissue or organ may be part of the subject's respiratory tract, gastrointestinal tract, salivary glands, cardiovascular system, liver, pancreas, bone marrow, joints, bones, cartilage, knee, skeleton, central nervous system or skin. Administration of the pharmaceutical composition may be topical, transdermal, mucosal, sub-mucosal, muscular, sub-muscular, by inhalation, parenteral or intravenous administration.

In other embodiments, provided herein are methods of managing or treating neonatal encephalopathy, traumatic brain injury or ischemia in a subject in need thereof, wherein the methods comprise administering to the subject a pharmaceutical composition that comprises the disclosed homogeneous human amniotic fluid clonal stem cell lines, thereby managing or treating neonatal encephalopathy, traumatic brain injury or ischemia in the subject.

In yet other embodiments, provided herein are methods of treating, controlling or managing diabetes in a subject with a damaged pancreas, wherein the methods comprise regenerating pancreatic islets by administering to the subject a pharmaceutical composition that comprises the disclosed homogeneous human amniotic fluid clonal stem cell lines, thereby treating, controlling or managing diabetes in the subject.

In additional embodiments, provided herein are methods of treating, controlling or managing a cardiovascular disease in a subject in need thereof, wherein the methods comprise regenerating cardiac tissue and vascularization by injecting into the subject's cardiac tissue a pharmaceutical composition that comprises the disclosed homogeneous human amniotic fluid clonal stem cell lines, thereby treating, controlling or managing the cardiovascular disease.

In yet other embodiments, provided herein are methods of treating, controlling or managing a progressive neurodegenerative disease in a subject in need thereof, wherein the methods comprise regenerating neurons by injecting into the subject's brain a pharmaceutical composition that comprises the disclosed homogeneous human amniotic fluid clonal stem cell lines, thereby treating, controlling or managing the progressive neurodegenerative disease. Progressive neurodegenerative diseases may include, but are not limited to, Alzheimer's disease, Huntington's disease, amyotrophic lateral sclerosis, multiple sclerosis, multiple system atrophy, or Parkinson's disease.

In additional embodiments, provided herein are methods of treating, controlling or managing muscular dystrophy in a subject in need thereof, wherein the methods comprise regenerating myogenic cells by administering to the subject a pharmaceutical composition that comprises the disclosed homogeneous human amniotic fluid clonal stem cell lines, thereby treating, controlling or managing muscular dystrophy.

Also provided herein are methods of managing, controlling or treating a peripheral nerve or muscle injury in a subject in need thereof, wherein the methods comprise parenterally administering to the subject a pharmaceutical composition that comprises the disclosed homogeneous human amniotic fluid clonal stem cell lines to regenerate the peripheral nerve or muscle, thereby managing, controlling or treating a peripheral nerve or muscle injury in the subject.

In other embodiments, provided herein are methods of regenerating skin, repairing a burn or healing a wound in a subject in need thereof, wherein the methods comprise topically or parenterally administering to the subject a pharmaceutical composition that comprises the disclosed homogeneous human amniotic fluid clonal stem cell lines, thereby regenerating the skin, repairing the burn or healing the wound in the subject.

In yet other embodiments, provided herein are methods of controlling, managing or treating arthritis in a subject in need thereof, wherein the methods comprise administering to the subject a pharmaceutical composition that comprises the disclosed homogeneous human amniotic fluid clonal stem cell lines, thereby controlling, managing or treating arthritis.

The pharmaceutical compositions administered by the disclosed methods may comprise one or more of a pharmaceutically acceptable excipient, pharmaceutically acceptable carrier, a diluent, adjuvant, stabilizer, emulsifier, preservative, colorant, or buffer. In some embodiments, the pharmaceutical compositions administered by the disclosed methods may optionally comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an antibacterial agent or an antifungal agent.

The methods disclosed herein provide effective autologous cell, tissue repair and tissue-engineered replacement treatment both in utero and in human subjects.

EXAMPLES

Example 1: Production of Homogeneous Human Amniotic Fluid Clonal Stem Cells

Amniotic fluid samples were collected from 10 pregnant human subjects at second semester amniocentesis. The amniotic fluid samples (2-5 ml for each sample) were diluted with PBS, and then centrifuged at 300 g (4° C.) for 5 minutes. The supernatant was discarded, and pelleted cells were resuspended in culture medium and transferred to 60 mm or 100 mm tissue culture dishes (Nunc Thermo Scientific, Hampton, New Hampshire). The dishes were incubated at 37° C. with 5% humidified $CO_2$ using complete AFSC medium consisting of MEM-alpha GlutaMAX (Life Technologies, Grand Island, New York), 20% Chang medium D (Irvine Scientific, Santa Ana, California), 15% embryonic stem cell-qualified fetal bovine serum (ES-FBS) (Life Technologies, Grand Island, New York), 100 µg/mL normocin (InvivoGen, San Diego, California). Cells were grown to ~70% of confluence in a 37° C. humidified incubator with 5% $CO_2$. Absence of *mycoplasma* in the culture was periodically verified with the Plasmotest kit (InVivogen San Diego). Cells were detached from plates using Accutase (MP Biomedicals, Irvine, California), and 30 samples were FACS sorted for CD90, SSEA4 and Tra-1-60. Aliquots at least 90% CD90 positive were then used to select a single cell for further passaging in 96 well plates. Tissue quality, round bottom 96-well plates (BD Falcon, Franklin Lakes, New Jersey) were coated with thin layer of 0.8% low melting agarose (Sigma-Aldrich, St. Louis, Missouri) dissolved in alpha-MEM-GlutaMAX by filling the wells with the melted agarose and then removing the fluid and allowing the remaining film of agarose to solidify during a brief incubation [~5 minutes] at 4° C. Cells were seeded at a concentration of 1 cell in 100 µl to each coated well. The plates were incubated in 37° C. incubator with 5% $CO_2$ for 2 days. Spheroids thus obtained were transferred into receiving wells of a 24-well flat-bottomed tissue culture plate (BD Falcon, Franklin Lakes, New Jersey) using wide bore pipette tips. The FACS sorting was repeated until consistent expression of CD90 exceeded 95% while SSEA4 and Tra 1-60 expression dropped to lower levels and remained consistent. After the cultures remained stable, the four most consistent and viable cultures were selected for differentiation studies and further characterization by FACS for other surface markers and nuclear transcription factors. Other stem cell markers identified were Oct-4, Sox-2, Nanog, Rex-1, CD117, 15, 44, 29, 9, 73 and 133.

Respective differentiation media were added to each well and the plates were incubated at 37° C. in a 5% $CO_2$ atmosphere for 2-3 weeks. After assessing differentiability, the two selected clones showed 99% CD90, 27% SSEA4, and 5-10% Tra-1-60 consistently expressed after 5 passages.

The other stem cell markers Oct-4, Sox-2, Nanog, Rex-1, CD117, 15, 44, 29, 9, 73 and 133 were expressed as well.

Example 2: In Vitro Differentiation of Homogeneous Human Amniotic Fluid Clonal Stem Cells and Pharmacological Agent Screening A. In Vitro Neural Differentiation STEMDIFF™ Neural Induction medium (Stemcell Technologies, Vancouver, Canada) is used to differentiate the disclosed homogeneous human amniotic fluid clonal stem cells toward a neuronal lineage. Spheroids are transferred into STEMDIFF Neural Induction medium supplemented with 10 mM Y-27632 ROCK inhibitor (Stem-Gent, Cambridge, MA), five spheroids per well, and differentiated for 21 days under the following conditions: unexposed to medication, single exposure to medication, and continuous exposure to medication, in addition to uninduced controls. The spheroids are fixed with 3.5% buffered formalin (Thermo Fisher Scientific, Hampton, NH) and incubated with 1:100 dilutions of the following monoclonal antibodies: mouse-anti-human-Nestin-AlexaFluor647 (BD Pharmingen), mouse-anti-human B-tubulin III-AlexaFluor488 (BD Pharmingen) and mounted with VECTASHIELD Mounting Medium with DAPI (Vector Labs, Burlingame, CA), or mouse-anti-human glial fibrillary acidic protein (GFAP)-AlexaFluor488 (BD Pharmingen) and VECTASHIELD Mounting Medium with DAPI (Vector Laboratories, Burlingham, CA). Spheroids are visualized under fluorescence microscopy with a Nikon Eclipse TE2000-E (Nikon Instruments, Inc.) inverted microscope, and images are acquired with Nikon NIS-Elements Imaging Software BR 3.10. Images are analyzed and quantitated using ImageJ 1.47v (National Institutes of Health, Bethesda, MD).

B. In Vitro Osteocyte Differentiation

Nonhematopoietic OSTEODIFF™ Medium (Miltenyi Biotech, Cambridge, MA) is used to differentiate homogeneous human amniotic fluid clonal stem cells to osteocytes; $4.5 \times 10^4$ spheroids are used in each assay (1 assay=1 well of a 6-well tissue culture plate) (BD Falcon). Differentiation is carried out for 10 days with medium changes every 2-3 days. The spheroids are transferred to osteocyte induction medium and incubated for 2 weeks. Differentiation is performed with samples unexposed to medication, single exposure to medication, and continuous exposure to medication, in addition to uninduced controls. Spheroids are either fixed with cold methanol and stained with SIGMA FAST BCIP/NBT (Sigma-Aldrich) for alkaline phosphatase-producing cells, or fixed with 3.7% buffered formalin for 30 min at room temperature and stained with 2% Alizarin Red solution pH4.3 (Sigma-Aldrich) for 45 minutes in the dark at room temperature. Spheroids are visualized under bright-field and phase-contrast microscopy as above. Osteogenic induction patterns are then studied under the same conditions with Ab83369 (Abcam, Cambridge, MA), a quantitative, alkaline, phosphatase, enzymatic colorimetric assay for analysis.

C. In Vitro Chondrocyte Differentiation

Nonhematopoietic OSTEODIFF™ Medium (Miltenyi Biotech, Cambridge, MA) is used to differentiate homogeneous human amniotic fluid clonal stem cells to chondrocytes. The spheroids are transferred to a 4-well chamber slide, five spheroids per well, under the following medium conditions: unexposed to medication, single exposure to medication, and continuous exposure to medication, in addition to non-induced controls. The spheroids are incubated for 21 days, with medium changes every 2-3 days. The spheroids are fixed in 3.5% buffered formalin (Thermo Fisher Scientific) and incubated with 1:100 dilutions of the primary monoclonal antibody, mouse anti-human Aggrecan antibody (Invitrogen, Carlsbad, CA), and 1:200 dilution of the secondary AlexaFluor594 goat anti-Rabbit IgG (H+L) antibody (Invitrogen). Coverslips are mounted with VECTASHIELD Mounting Medium with DAPI (Vector Laboratories). Spheroids are visualized under fluorescence microscopy with a Nikon Eclipse TE2000-E (Nikon Instruments, Inc.) inverted microscope and images are acquired with Nikon NIS-Elements Imaging Software BR 3.10. Images are analyzed and quantitated using ImageJ 1.47v (National Institutes of Health).

D. Genomic Characterization

Samples from each subject are either left untreated, treated with valproic acid (VPA, a known teratogen), or treated with dexamethasone (DEX, promotes fetal maturation), or treated with $MgSO_4$ (administered in pregnancy for seizure prophylaxis and fetal neuroprotection). All cells are harvested and RNA collected through the RNeasy Mini Kit (Qiagen, Valencia, CA). A NanoDrop Spectrophotometer (ND200) (Thermo Fisher Scientific, Springfield Township, NJ) is used to determine concentration and purity. Gene expression analysis is performed using the Affymetrix method of expression analysis, principal component analysis (PCA) for gene expression. The Affymetrix Expression Console software is used to extract expression data from each microarray chip using the robust multiarray average algorithm. Data are imported into the R statistical programming environment. The R/Bio-conductor package, Limma (Linear Models for Microarray Data, version 3.22.3), is used to assess the quality of the data and to analyze for differential expression after control and low expressing probes are filtered from the data set.

E. Statistical Analysis

The cells of each sample are separately analyzed by ImageJ for chondrogenic and neural differentiation studies. For osteogenic induction, samples are analyzed by Ab83369 (Abcam). At least five cells are used for each sample and each analysis is done in triplicate. Mean and standard deviation are calculated for results of induction for each assay. As the number of cells varies for each sample, an average of averages is calculated for reporting each condition. For genomic studies, enrichment score $\geq 2$, fold change $\geq 2.0$, and P value $<0.01$ are considered significant. Bonferroni and Benjamini corrections are applied and compared with the uncorrected data.

F. Genomic Analysis

PCA is employed to determine significant differences in gene expression between treated and untreated cell cultures. Database for Annotation, Visualization, and Integrated Discovery (DAVID) is utilized for cluster analysis to determine pertinent affected functions due to exposure to the agents studied. GOTERM FAT library is chosen to reflect gene ontology and biological processes. Ingenuity Pathway Analysis (IPA) (IPA®; Qiagen, Redwood City, CA) is utilized to analyze data identified by Affymetrix analysis for both VPA and DEX. Canonical pathways, network functions, and disease and pathway heat maps are generated and analyzed. All function results are coded to reflect either upregulation or downregulation and to reflect z-score.

G. Pharmacological Agent Effect

The effect of each pharmacological agent on the proliferation and differentiation of the disclosed homogeneous human amniotic fluid clonal stem cells, and on gene expression is evaluated. The results (not shown) show that DEX enhances cellular growth and neural and bone development in utero. VPA treatment does not affect osteogenic and chondrogenic differentiation, but it decreases neurological development. Treatment with $MgSO_4$ has minimal or no effect on osteogenic, chondrogenic and neurological development.

Example 3: Amniotic Fluid Stem Cell Clone-Mediated Allogeneic Skin Graft

Amniotic fluid stem cells (AFSC) have immunomodulatory and anti-inflammatory properties. An experimental study was performed to determine if application of AFSCs in a collagen matrix on transplanted skin facilitate tolerance of skin grafts.

Materials

Six to eight week old black C57B1/6 mice and six to eight week old black Balb/c mice were used as recipients of skin grafts. Each group of mice included five animals. For each group, three animals were experimental and two animals were used as vehicle control. The animals were anesthetized and the animals' backs were shaved and then a depilatory agent was applied to remove all hair. A 1.5-cm-diameter circular wound was inflicted on each animal, sterilized and coated with PURACOL®. White mice skin graft was applied to the 1.5 cm wound square template on each animal.

$7.2 \times 10^6$ $CD90^+$ amniotic fluid stem cloned cells were prepared, stained with 1,1'-Dioctadecyl-3,3,3',3'-Tetramethylindocarbocyanine Perchlorate (DiI) and applied to each graft side of the experimental animals. Placebo was applied to each graft side of the vehicle control animals. In a first set of 10 mice the cloned cells were applied topically, and in a second set of 10 mice the cloned cells were injected subcutaneously around each graft.

The treated mice were observed at post-operative day (POD) 5 and and at POD 7 for signs of rejection, such as edema and/or erythema. At POD 7, tissues were collected from one control and one experimental mice for each group in each set. The tissues were formalin-fixed and paraffin-embedded, stained with hematoxylin and eosin, and optical coherence tomography (OCT) imaging was performed. The tissues were further stained with CD11B or F480, C4d, and CD68 to observe acute rejection and photographed every POD.

Vehicle control mice rejected their grafts by POD 10 or POD 11 (Data not shown). In contrast, experimental mice treated with the cloned cells showed no signs of rejection before day 14, and most clone-treated grafts lasted 21 days, 10 days longer than vehicle control mice. These results demonstrated that the cloned amniotic fluid stem cells induced significant graft tolerance. The experimental black mice treated with the cloned cells also showed a healthy white graft and significant hair growth on the treated grafts, indicating enhanced vascularization. See FIG. 1.

Example 4: Treatment of Ischemia

A pharmaceutical composition comprising the disclosed homogeneous human amniotic fluid clonal stem cells is injected into the ischemic hind limbs of mice. The cells spontaneously differentiate into vascular-like structures and exhibit endothelial-specific genes and proteins. Engraftment rate is high, and implantation of the disclosed homogeneous human amniotic fluid clonal stem cells augments blood perfusion and capillary density, indicating neovascularization.

Example 5: In Vitro and In Vivo Regeneration of Skeletal Muscle

One or more clones of the disclosed homogeneous human amniotic fluid clonal stem cells are co-cultured in vitro with C2C12 myoblasts. Differentiation analysis shows that the cells differentiate into skeletal myogenic cells, and express skeletal myogenic cell-specific markers such as Desmin, Troponin I (Tn I) and α-Actinin.

A pharmaceutical composition comprising the disclosed homogeneous human amniotic fluid clonal stem cells is injected into cardiotoxin-injured and X-ray-irradiated tibialis anterior (TA) muscles of NOD/SCID mice. The cells differentiate into myogenic precursor cells and fuse with host myofibres.

Example 6: Biodegradable Scaffolds for Tissue Repair

The disclosed homogeneous human amniotic fluid clonal stem cells are proliferated in a chondrogenic medium containing transforming growth factor-beta2 (TGF-beta2) and insulin growth factor-1 (IGF-1) for 6-12 weeks. The cells are then seeded onto a biodegradable polyglycolic acid scaffold and maintained in the same chondrogenic medium within a rotating bioreactor for 10-15 weeks to produce a tendon graft. The engineered scaffold is surgically inserted into a lamb for diaphragmatic hernia repair. Examination shows evidence of chondrocyte differentiation and regeneration of cartilage.

Example 7: Effect of Homogeneous Human Amniotic Fluid Clonal Stem Cells in Subjects with Moderate-to-Severe Alzheimer's Disease The superiority of efficacy and safety of pharmaceutical compositions containing the disclosed homogeneous human amniotic fluid clonal stem cells compared to placebo is assessed for treatment of signs and symptoms in subjects with moderate-to-severe Alzheimer's disease.

The disclosed pharmaceutical compositions are injected into the subjects' brain in two initial doses at days 1 and 15. This experimental regimen is compared to a same regimen where a pharmaceutical composition containing placebo is administered in place of the disclosed homogeneous human amniotic fluid clonal stem cells. 10 subjects are included in each of the two groups. Subjects are monitored for disease activity and symptoms, such as confusion and forgetfullness, over a period of one year.

At the end of the one year period, subjects treated with the disclosed pharmaceutical compositions show a significant improvement of symptoms and indicators of Alzheimer's disease over the control.

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

What is claimed is:

1. A method of regenerating tissue, repairing a burn or healing a wound in a subject in need thereof, wherein the method comprises topically or parenterally administering to a tissue, burn or wound a pharmaceutical composition that comprises a therapeutically effective amount of a homogeneous human amniotic fluid clonal stem cells, wherein at least 95% of the homogenous human amniotic fluid clonal stem cells express CD90 after each passage of the homogenous human amniotic fluid clonal stem cell lines through a total of five passages or more before administration of the pharmaceutical composition to a tissue, burn or wound.

2. The method of claim 1, wherein the pharmaceutical composition further comprises a diluent, adjuvant, stabilizer, emulsifier, preservative, colorant or buffer.

3. The method of claim 1, wherein the pharmaceutical composition further comprises one or more of a chemotherapeutic agent, an immunosuppressive agent, an immune-stimulatory agent, an antipyretic agent, a cytotoxic agent, a nucleolytic compound, a radioactive isotope, a receptor, a pro-drug activating enzyme, an anti-inflammatory agent, an antibiotic, a protease inhibitor, a growth factor, an antibacterial agent or an antifungal agent.

4. The method of claim 1, wherein the tissue is one or more of tissue from respiratory tract, gastrointestinal tract, salivary glands, cardiovascular system, liver, pancreas, bone marrow, joints, bones, cartilage, muscles, knee, skeleton, central nervous system or skin.

5. The method of claim 1, further comprising a step of inducing differentiation of the homogeneous human amniotic fluid clonal stem cells with a biodegradable scaffold.

6. The method of claim 1, wherein the human amniotic fluid clonal stem cells differentiate into different cells in the wound or burn.

7. The method of claim 1, wherein after a total of five or more passages before administration of the pharmaceutical composition to a tissue, burn or wound, 27% of the amniotic fluid clonal stem cells also express SSEA4 and 5-10% of the amniotic fluid clonal stem cells also express TRA-1-60.

8. The method of claim 1, wherein the amniotic fluid clonal stem cells express Oct-4, Sox-2, Nanog, Rex-1, CD117, CD15, CD44, CD29, CD9, CD73 and CD133 after a total of five or more passages before administration of the pharmaceutical composition to a tissue, burn or wound.

9. The method of claim 1, wherein an application of the pharmaceutical composition results in a healthy graft.

10. The method of claim 1, wherein a wound cleansing agent is administered to the wound prior to administration of the pharmaceutical composition.

* * * * *